US008545412B2

(12) United States Patent
Kim et al.

(10) Patent No.: US 8,545,412 B2
(45) Date of Patent: Oct. 1, 2013

(54) SYSTEMS AND METHODS FOR MAKING AND USING IMAGE-GUIDED INTRAVASCULAR AND ENDOCARDIAL THERAPY SYSTEMS (75) Inventors: Grace Kim, Minneapolis, MN (US); Tat-Jin Teo, Sunnyvale, CA (US); Barbara Huibregtse, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1160 days.

(21) Appl. No.: 12/475,179

(22) Filed: May 29, 2009

(65) Prior Publication Data

US 2010/0305451 A1    Dec. 2, 2010

(51) Int. Cl.
*A61B 8/00* (2006.01)
*A61B 6/00* (2006.01)

(52) U.S. Cl.
USPC .......................................... 600/463; 600/459

(58) Field of Classification Search
USPC ........................................................ 600/439
See application file for complete search history.

(56) References Cited

U.S. PATENT DOCUMENTS

| 4,043,181 A * | 8/1977 | Nigam ............................. 73/614 |
| 4,057,049 A | 11/1977 | Hill |
| 4,063,549 A | 12/1977 | Beretsky et al. |
| 4,350,917 A | 9/1982 | Lizzi et al. |
| 4,484,569 A | 11/1984 | Driller et al. |
| 4,550,607 A | 11/1985 | Maslak et al. |
| 4,561,019 A | 12/1985 | Lizzi et al. |
| 4,662,380 A | 5/1987 | Riley |
| 4,817,015 A | 3/1989 | Insana et al. |
| 4,858,124 A | 8/1989 | Lizzi et al. |
| 4,932,414 A | 6/1990 | Coleman et al. |

(Continued)

FOREIGN PATENT DOCUMENTS

| DE | 4439796 C1 | 4/1996 |
| EP | 3595 A2 | 8/1979 |

(Continued)

OTHER PUBLICATIONS

International Search Report and Written Opinion mailed Sep. 15, 2010 for International Patent Application No. PCT/US2010/035944.

(Continued)

*Primary Examiner* — Tse Chen
*Assistant Examiner* — Patricia Park
(74) *Attorney, Agent, or Firm* — Frommer Lawrence & Haug LLP; Patrick R. Turner (57) ABSTRACT

A catheter assembly includes a catheter and a delivery element. The catheter has a distal end with a distal tip, a proximal end, and a longitudinal length. The catheter includes a body that defines a central lumen extending along the catheter to the distal end. The catheter also includes a forward-facing transducer array disposed at the distal tip of the catheter. The transducer array is configured and arranged for transforming applied electrical signals to acoustic signals and also for transforming received echo signals to electrical signals. At least one catheter conductor is electrically coupled to the transducer array and extends along the catheter. The delivery element is disposed in the lumen of the catheter. The delivery element includes a distal tip that is configured and arranged for contacting patient tissue. The distal tip of the delivery element is configured and arranged to extend beyond the distal tip of the catheter.

12 Claims, 6 Drawing Sheets

(56) References Cited

U.S. PATENT DOCUMENTS

| | | | |
|---|---|---|---|
| 4,945,478 A | 7/1990 | Merickel et al. | |
| 4,982,339 A | 1/1991 | Insana et al. | |
| 5,016,615 A | 5/1991 | Driller et al. | |
| 5,125,410 A | 6/1992 | Misono et al. | |
| 5,193,546 A | 3/1993 | Shaknovich | |
| 5,224,480 A | 7/1993 | Yamada et al. | |
| 5,257,624 A | 11/1993 | Fraser et al. | |
| 5,293,871 A | 3/1994 | Reinstein et al. | |
| 5,335,184 A | 8/1994 | Hildebrand | |
| 5,375,470 A | 12/1994 | Matsushima et al. | |
| 5,417,215 A | 5/1995 | Evans et al. | |
| 5,477,858 A | 12/1995 | Norris et al. | |
| 5,485,845 A | 1/1996 | Verdonk et al. | |
| 5,501,221 A | 3/1996 | Foster et al. | |
| 5,579,768 A | 12/1996 | Klesenski | |
| 5,640,961 A | 6/1997 | Verdonk | |
| 6,024,703 A * | 2/2000 | Zanelli et al. | 600/437 |
| 6,039,689 A | 3/2000 | Lizzi | |
| 6,050,947 A | 4/2000 | Rhyne et al. | |
| 6,095,976 A | 8/2000 | Nachtomy et al. | |
| 6,102,859 A | 8/2000 | Mo | |
| 6,120,445 A | 9/2000 | Grunwald | |
| 6,120,446 A | 9/2000 | Ji et al. | |
| 6,142,940 A | 11/2000 | Lathbury et al. | |
| 6,154,560 A | 11/2000 | Cothren et al. | |
| 6,159,153 A | 12/2000 | Dubberstein et al. | |
| 6,186,951 B1 | 2/2001 | Lizzi et al. | |
| 6,238,342 B1 | 5/2001 | Feleppa et al. | |
| 6,263,094 B1 | 7/2001 | Rosich et al. | |
| 6,287,259 B1 | 9/2001 | Grunwald | |
| 6,312,383 B1 | 11/2001 | Lizzi et al. | |
| 6,423,007 B2 | 7/2002 | Lizzi et al. | |
| 6,514,202 B2 | 2/2003 | Grunwald | |
| 6,579,238 B1 | 6/2003 | Simopoulos et al. | |
| 6,585,655 B2 * | 7/2003 | Crowley | 600/463 |
| 6,592,520 B1 | 7/2003 | Peszynski et al. | |
| 6,621,341 B1 | 9/2003 | Shifrin | |
| 6,743,174 B2 | 6/2004 | Ng et al. | |
| 6,767,338 B2 | 7/2004 | Hawk et al. | |
| 6,945,938 B2 | 9/2005 | Grunwald | |
| 7,306,561 B2 | 12/2007 | Sathyanarayana | |
| 2002/0087218 A1 | 7/2002 | Amemiya | |
| 2003/0023393 A1 | 1/2003 | Oravecz | |
| 2004/0002435 A1 | 1/2004 | Petersen et al. | |
| 2004/0006273 A1 | 1/2004 | Kim et al. | |
| 2004/0039286 A1 | 2/2004 | Kuban et al. | |
| 2006/0100522 A1 | 5/2006 | Yuan et al. | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2007/0135887 A1 | 6/2007 | Maschke | |
| 2008/0097476 A1 * | 4/2008 | Peh et al. | 606/130 |
| 2008/0221448 A1 | 9/2008 | Khuri-Yakub et al. | |
| 2009/0030276 A1 | 1/2009 | Saadat et al. | |
| 2009/0030312 A1 | 1/2009 | Hadjicostis | |
| 2009/0088648 A1 | 4/2009 | Jaffe et al. | |

FOREIGN PATENT DOCUMENTS

| | | |
|---|---|---|
| EP | 0459813 A2 | 12/1991 |
| EP | 0696435 A2 | 2/1996 |
| GB | 2319841 A | 6/1998 |
| WO | WO-9201932 A1 | 2/1992 |
| WO | WO-9423652 A1 | 10/1994 |
| WO | WO-9628096 A1 | 9/1996 |
| WO | WO-0182787 A2 | 11/2001 |
| WO | WO-03083506 A1 | 10/2003 |
| WO | 2005046443 A2 | 5/2005 |
| WO | 2006110666 A2 | 10/2006 |
| WO | 2008046031 A2 | 4/2008 |
| WO | WO 2009/073752 * | 11/2008 |

OTHER PUBLICATIONS

Degertekin, F. Levent, et al., "Annular-Ring CMUT Arrays for Forward-Looking IVUS: Transducer Characterization and Imaging," IEEE Transactions on Ultrasonics, Ferroelectronics, and Frequency Control, vol. 53, No. 2, Feb. 13, 2006, pp. 474-482. http://ieeexplore.ieee.org/xpis/abs_all.jsp?arnumber=1593387.

Guldiken, Rasim, et al., "Dual-Annular-Ring CMUT Array for Forward-Looking IVUS Imaging," Ultrasonics Symposium, 2006, IEEE, Oct. 2, 2006-Apr. 16, 2007, pp. 698-701. http://ieeexplore.ieee.org/xpls/abs_all.jsp?arnumber=4152043.

* cited by examiner

SYSTEMS AND METHODS FOR MAKING AND USING IMAGE-GUIDED INTRAVASCULAR AND ENDOCARDIAL THERAPY SYSTEMS

TECHNICAL FIELD

The present invention is directed to the area of intravascular and endocardial therapy systems and methods of making and using the systems. The present invention is also directed to intravascular and endocardial therapy systems using intravascular ultrasound imaging for facilitating local delivery of therapy or of one or more therapeutic agents to a target therapy site.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to monitor or assess ongoing intravascular treatments, such as angioplasty and stent placement in real (or almost real) time. Moreover, IVUS imaging systems can be used to monitor one or more heart chambers, for example, a left ventricle.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are detected by the one or more transducers and transformed to electric pulses. The transformed electric pulses are delivered to the image processor and converted to an image displayable on the monitor.

Intravascular and endocardial therapy devices (e.g., endocardial direct injection systems, or the like) have been developed to provide a way to deliver one or more therapeutic agents to patient vasculature or endocardial regions to treat symptoms related to many different diseases and disorders (e.g., coronary heart disease, or the like). An intravascular and endocardial therapy device can include a catheter and a delivery element (e.g., a needle, trocar, or the like) in fluid communication with a therapeutic source. The catheter can be inserted into patient vasculature and, for example, positioned within the left ventricle of the heart such that the delivery element can be extended along the catheter to provide local intervention at the vessel wall, or heart wall, or inserted into a wall of the left ventricle to deliver the therapeutic agent to patient tissue. Alternately, or additionally, the delivery element can also deliver a therapeutic agent without piercing patient tissue. Alternately, or additionally, the therapeutic agent can be delivered to other intravascular or endocardial regions of the patient, as well.

BRIEF SUMMARY

In one embodiment, a catheter assembly includes a catheter and a delivery element. The catheter has a distal end with a distal tip, a proximal end, and a longitudinal length. The catheter includes a body that defines a central lumen extending along the catheter to the distal end. The catheter also includes a forward-facing transducer array disposed at the distal tip of the catheter. The transducer array is configured and arranged for transforming applied electrical signals to acoustic signals and also for transforming received echo signals to electrical signals. At least one catheter conductor is electrically coupled to the transducer array and extends along the catheter. The delivery element is disposed in the lumen of the catheter. The delivery element includes a distal tip that is configured and arranged for contacting patient tissue. The distal tip of the delivery element is configured and arranged to extend beyond the distal tip of the catheter.

In another embodiment, an intravascular and endocardial therapy system includes a catheter, a delivery element, and a control module. The catheter has a distal end with a distal tip, a proximal end, and a longitudinal length. The catheter includes a body that defines a central lumen extending along the catheter to the distal end. The catheter also includes a forward-facing transducer array disposed at the distal tip of the catheter. The transducer array is configured and arranged for transforming applied electrical signals to acoustic signals and also for transforming received echo signals to electrical signals. At least one catheter conductor is electrically coupled to the transducer array and extends along the catheter. The delivery element is disposed in the lumen of the catheter. The delivery element includes a distal tip that is configured and arranged for contacting patient tissue. The distal tip of the delivery element is configured and arranged to extend beyond the distal tip of the catheter. The control module is coupled to the transducer array. The control module includes a pulse generator and a processor. The pulse generator is configured and arranged for providing electric signals to the transducer array. The pulse generator is electrically coupled to the transducer array via the at least one catheter conductor. The processor is configured and arranged for processing received electrical signals from the transducer array to form at least one image. The processor is electrically coupled to the transducer array via the at least one catheter conductor.

In yet another embodiment, a method for performing an intravascular or endocardial therapy procedure includes inserting a catheter assembly into a blood vessel of a patient. The catheter assembly includes a catheter defining a lumen and a delivery element having a distal tip disposed in the lumen. The catheter includes a forward-facing transducer array disposed at a distal tip of the catheter. The catheter is guided through patient vasculature such that the distal tip of the delivery element is in proximity to a target therapy site. At least one image of the target therapy site is generated using the transducer array. A distal tip of the delivery element is inserted into patient tissue at the target therapy site. A dose of a therapeutic agent is drawn from a therapeutic source through the delivery element to the target therapy site.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular and endocardial therapy systems and methods of making and using the systems. The present invention is also directed to intravascular and endocardial therapy systems using intravascular ultrasound imaging for facilitating local delivery of therapy or of one or more therapeutic agents to a target therapy site.

Suitable intravascular and endocardial therapy systems include, but are not limited to, a catheter configured and arranged for delivering therapy or one or more therapeutic agents to a target intravascular or endocardial therapy site, the catheter including one or more IVUS imaging transducers disposed on a distal end of the catheter and coupled to a control module. Examples of therapy catheters configured and arranged to deliver therapy or one or more therapeutic agents to a target therapy site are found in, for example, U.S. Pat. No. 6,767,338. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
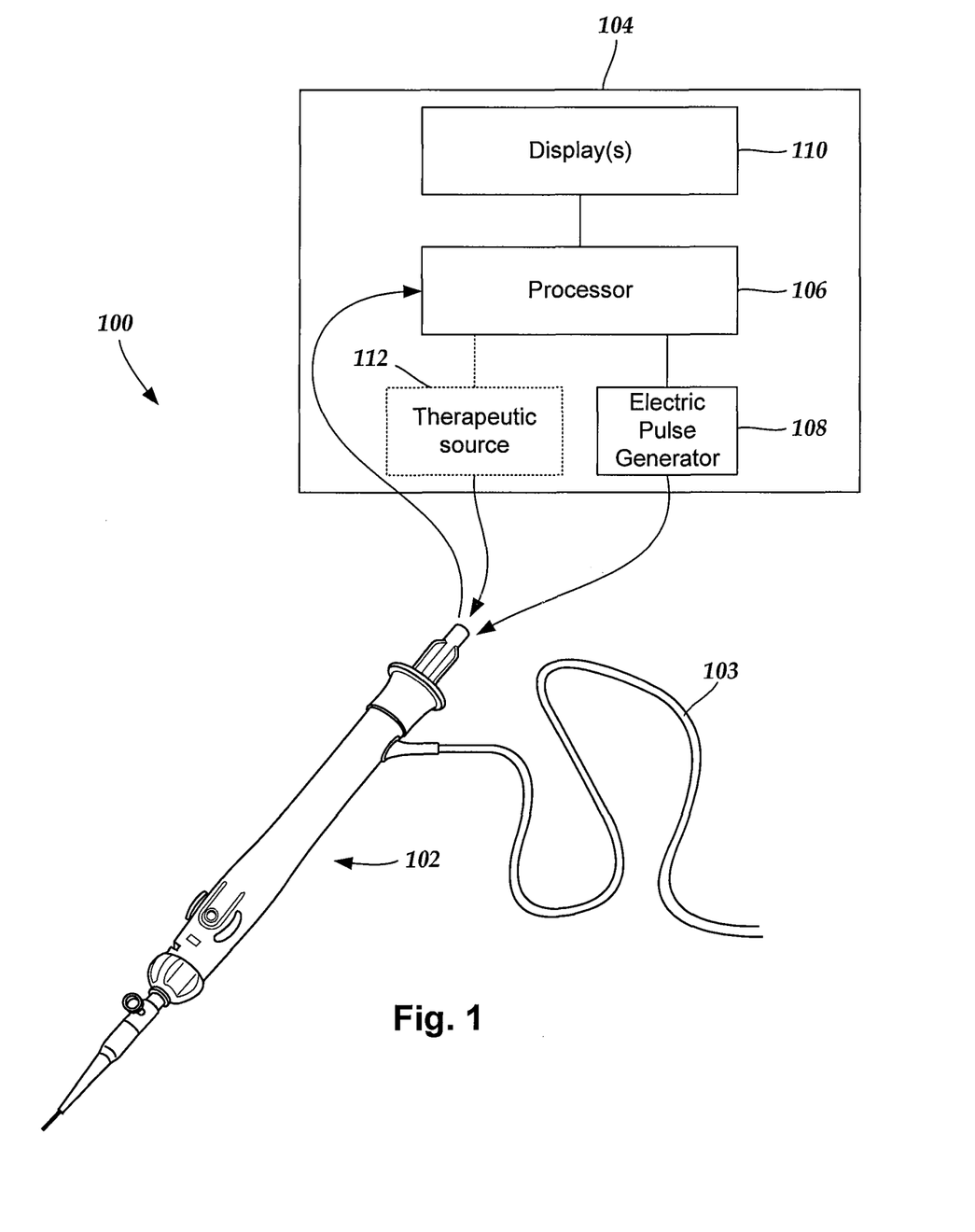
FIG. 1 is a schematic view of one embodiment of an intravascular or endocardial therapy system that includes a catheter and a control module, according to the invention.

FIG. 1 illustrates schematically one embodiment of an intravascular and endocardial therapy system 100. The intravascular and endocardial therapy system 100 includes a catheter 102 that is coupleable to a control module 104. The catheter includes a side manifold port through which a portion of a connection wire 103 extends. The control module 104 may include, for example, a processor 106, a pulse generator 108, and one or more displays 110. In at least some embodiments, the pulse generator 108 forms electric pulses that may be input to one or more transducers (310 in FIG. 3A) disposed on the catheter 102. In at least some embodiments, electric pulses transmitted from the one or more transducers (310 in FIG. 3A) may be input to the processor 106 for processing. In at least some embodiments, the processed electric pulses from the one or more transducers (310 in FIG. 3A) may be displayed as one or more images on the one or more displays 110. In at least some embodiments, the processor 106 may also be used to control the functioning of one or more of the other components of the control module 104. For example, the processor 106 may be used to control at least one of the frequency or duration of the electrical pulses transmitted from the pulse generator 108 or one or more properties of one or more images formed on the one or more displays 110.

In at least some embodiments, the control module 104 may also include a therapeutic source 112. In at least some embodiments, the therapeutic source 112 is used to control supply and deliver one or more controlled doses of one or more therapeutic agents to a patient via a delivery element (308 in FIG. 3A) at least partially disposed in the catheter 102. In at least some embodiments, the processor 106 may also be used to control the delivery of the one or more therapeutic agents. In at least some embodiments, the therapeutic source 112 operates separately and independently from the control module 104.

Many different therapeutic agents (e.g., inotropic agents, ACE inhibitors, angiogenic agents, cells (e.g., stem cells, or the like), NSAIDS and other anti-inflammatory agents, sclerotic agents, or the like or combinations thereof) may be used to treat many different diseases or disorders including, for example, diffuse myocardial disease, pulmonary vein ablation, atherosclerotic lesions, or the like. Delivering one or more therapeutic agents locally (via the intravascular and endocardial therapy system 100) may increase the therapeutic value of the therapeutic agents by localizing dosages. Also, local delivery of a therapeutic agent may reduce the amount of therapeutic agent used, as compared to systemic delivery, to provide equivalent therapeutic value to the patient. Moreover, local delivery of a therapeutic agent may reduce the risk of the patient having an adverse effect from the therapeutic agent, as compared to systemic delivery, due to a more limited region of delivery.

In at least some embodiments, an intravascular and endocardial therapy procedure may involve delivering a therapeutic agent to a target therapy site at an intravascular or endocardial region (e.g., a wall of the left atrium of a patient heart) of a patient. One exemplary intravascular and endocardial therapy procedure involves inserting a catheter into the left ventricle of the heart, piercing a wall of the left ventricle, and locally delivering one or more therapeutic agents into the wall via the delivery element. During an intravascular and endocardial therapy procedure it is important to not completely penetrate walls during therapeutic agent delivery. For example, when piercing the wall of a left ventricle, complete penetration of the wall may lead to blood flow into the pericardium which may cause tamponade. Accordingly, it is preferable to avoid piercing regions of the wall that may be too thin to be safely pierced.

Currently, at least some intravascular and endocardial therapy procedures use radiopaque markers disposed on a catheter to guide the delivery element to a target therapy site. Unfortunately, radiopaque markers may not provide much, if any, information about the target therapy site. For example, when the target therapy site is a wall of the left ventricle, the radiopaque markers may not provide information about the thickness of the wall or the location on the wall where the delivery element is to be inserted.

Figure 2:
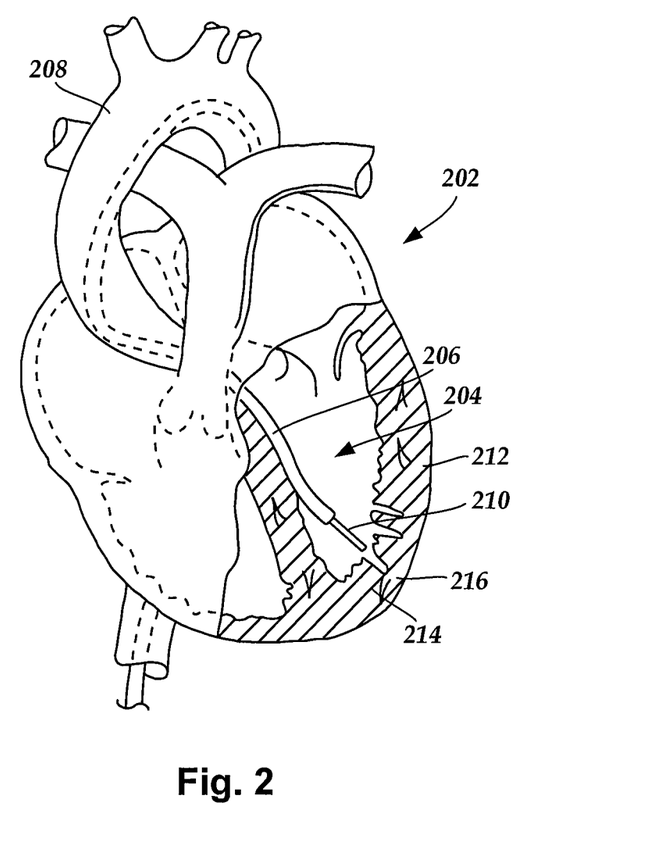
FIG. 2 is a schematic perspective view of a human heart with a cutaway view of the left ventricle of the heart, a portion of the catheter of FIG. 1 is shown inserted through patient vasculature such that a distal portion of the catheter is disposed in the left ventricle, according to the invention.

FIG. 2 is a schematic perspective view of a human heart 202 with a cutaway view of the left ventricle 204 of the heart 202. A catheter 206 is extended through patient vasculature 208 such that a delivery element 210 disposed in the catheter 206 is positioned in proximity to a wall 212 of the left ventricle 204. In FIG. 2, the delivery element 210 is shown extending from a distal tip of the catheter 206 and is configured and arranged to pierce patient tissue within the wall 212 and deliver one or more therapeutic agents to the wall 212.

The wall 212 of the left ventricle 204 may not have a uniform thickness. For example, sometimes the wall 212 may have one or more relatively thick regions, such as region 214, or one or more relatively thin regions, such as region 216. The location of the delivery may be determined based on the location of an infarct, which may be on either a relatively thin region or a relatively thick region. When possible, it is generally preferred to deliver the one or more therapeutic agents to a region of the wall 212 that is thick enough to be pierced without undue risk of completely penetrating the wall 212.

An intravascular and endocardial therapy system is described that incorporates IVUS imaging to the catheter of an intravascular and endocardial therapy system. In at least some embodiments, the IVUS imaging is used for facilitating guidance of the delivery element to a target therapy site. In at least some embodiments, the IVUS imaging is used to detect when a delivery element of the intravascular and endocardial therapy system contacts patient tissue. In at least some embodiments, the IVUS imaging is used to provide information for improving selection of the location of the target therapy site. In at least some embodiments, the information for improving selection of the location of the target therapy site includes information on the thickness of a wall of tissue in which the delivery element is to be inserted. In at least some embodiments, the information for improving selection of the location of the target therapy site includes information on one or more other germane characteristics of the wall of tissue in which the delivery element is to be inserted (e.g., regions of infarct, fibrosis, or the like).

Figure 3A:
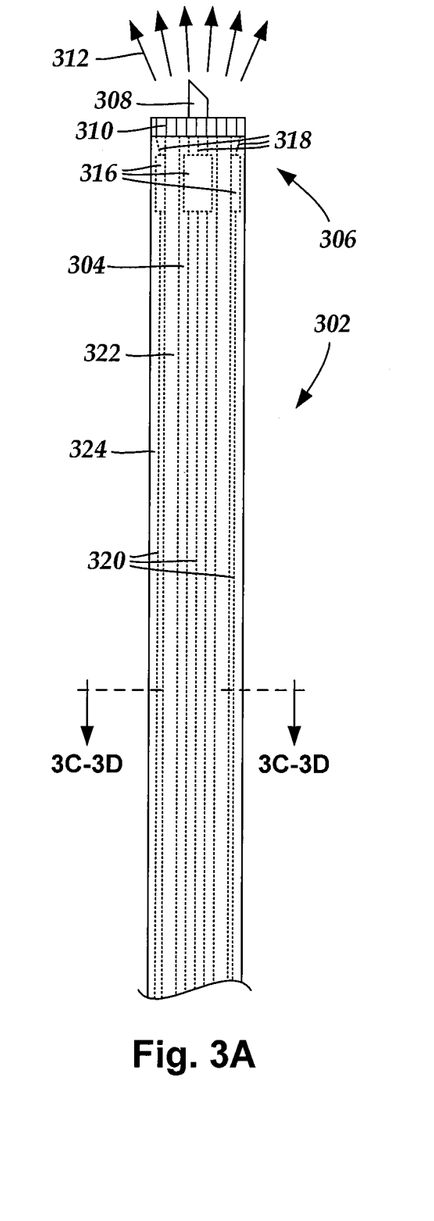
FIG. 3A is a schematic side view of one embodiment of a delivery element extending through a medial portion of a catheter and extending from a distal end of the catheter, according to the invention.
Figure 3B:
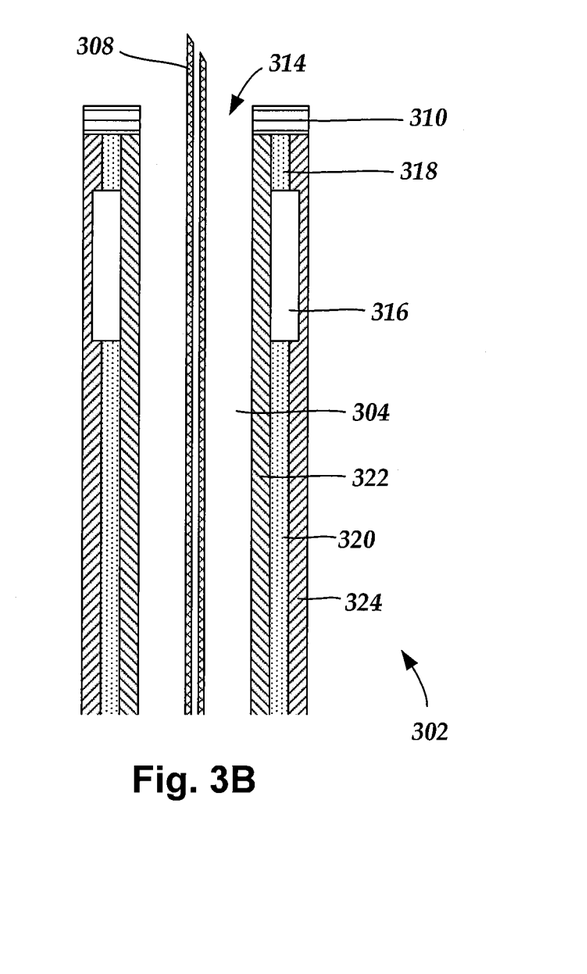
FIG. 3B is a schematic longitudinal cross-sectional view of one embodiment of a distal portion of the catheter of FIG. 3A, according to the invention.
Figure 3C:
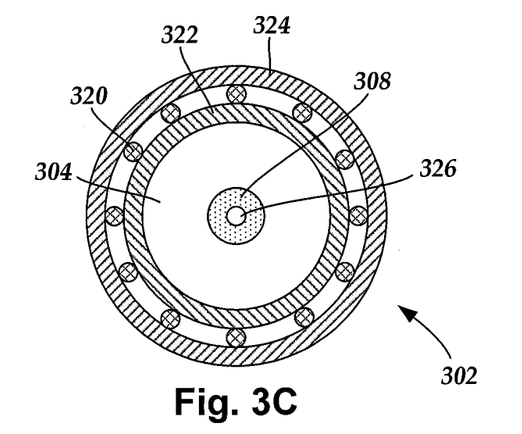
FIG. 3C is a schematic transverse cross-sectional view of one embodiment of a medial portion of the catheter of FIG. 3A, according to the invention.

FIG. 3A is a schematic side view of one embodiment of a medial portion and a distal end of a catheter 302. FIG. 3B is a schematic longitudinal cross-sectional view of one embodiment of the distal end of the catheter 302. FIG. 3C is a schematic transverse cross-sectional view of one embodiment of the medial portion of the catheter 302. The catheter 302 defines a lumen 304 extending along a longitudinal axis from a distal tip 306 of the catheter 302. A delivery element 308 is disposed in the lumen 304 and extends from the distal tip 306 of the catheter 302. The catheter 302 includes an ultrasound transducer array 310 disposed at the distal tip 306 of the catheter 302. In at least some embodiments, the transducer array 310 is forward-facing, such that energy is transmitted in a direction shown by directional arrows 312. In at least some embodiments, the transducer array 310 is annular. In at least some embodiments, the annular transducer array 310 forms a center aperture 314 that at least partially aligns with a distal end of the lumen 304. In at least some embodiments, the delivery element 308 is configured and arranged to extend through the center aperture 314 of the transducer array 310.

By orienting the transducer array 310 such that acoustic signals are emitted in a forward direction, the transducer array 310 can be used to guide the catheter 302 in real time. In at least some embodiments, the transducer array 310 can also be used to determine the thickness of objects positioned in front of the catheter 302. For example, in at least some embodiments, the transducer array 310 can image a wall of a left ventricle as the delivery element 308 is guided to a target therapy site along the wall of the left ventricle.

In at least some embodiments, the transducer array 310 includes a plurality of imaging elements. The transducer array 310 can contain any number of imaging elements. In at least some embodiments, capacitive micromachined ultrasonic transducer ("cMUT") elements are used. In at least some embodiments, the transducer array 310 is electrically coupled to integrated circuits 316 configured and arranged to perform image processing by transducer conductors. In at least some embodiments, the integrated circuits 316 are disposed on the catheter 302 proximal to the transducer array 310. In at least some embodiments, the integrated circuits 316 are electrically coupled to the control module (104 in FIG. 1) via catheter conductors 320.

In at least some embodiments, the catheter 302 includes a body that includes two or more layers of material. In at least some embodiments, as shown in FIGS. 3B and 3C, the catheter 302 includes an inner layer 322 and an outer layer 324. In some embodiments, the inner layer 322 and the outer layer 324 are formed from the same material. In at least some embodiments, the inner layer 322 and the outer layer 324 are formed from different materials. In at least some embodiments, the transducer array 310 is disposed on an outer surface of the inner layer 322 of material. In at least some embodiments, one or more of the integrated circuits 316 are disposed on an outer surface of the inner layer 322 of material. In at least some embodiments, one or more of the catheter conductors 320 are disposed on the outer surface of the inner layer 322 of material. In at least some embodiments, the transducer array 310 is bonded (e.g., using one or more adhesives, or the like) to the inner layer 322. In at least some embodiments, one or more of the integrated circuits 316 are bonded (e.g., using one or more adhesives, or the like) to the inner layer 322. In at least some embodiments, the outer layer 324 secures one or more of the catheter conductors 320 along at least a portion of the longitudinal length of the catheter 302. In alternate embodiments, one or more of the catheter conductors 320 are disposed in the lumen 304.

In at least some embodiments, a multiplexer and a demultiplexer can be used to control selective transmission of signals between the control module (104 in FIG. 1) and a relatively-large number of imaging elements of the transducer array 310 along shared catheter conductors 320, thereby allowing for a reduced number of catheter conductors 320 needed to be extended along the longitudinal length of the catheter 302. In at least some embodiments, an outer diameter of the transducer array 310 is flush with an outer diameter of the outer layer 324 of material.

The inner layer 322 may be formed from any flexible, biocompatible material suitable for insertion into a patient. Examples of suitable materials include, for example, polyethylene, polyurethane, plastic, nitinol hypotube, and the like or combinations thereof. The outer layer 324 may be formed from many different flexible biocompatible materials including, for example, one or more heat shrinkable materials (e.g., fluorinated ethylene propylene, polytetrafluoroethylene, or the like or combinations thereof).

The delivery element 308 is disposed in the lumen 304 of the catheter 302. In at least some embodiments, the delivery element 308 defines one or more lumens 326 configured and arranged to deliver one or more therapeutic agents from the therapeutic source (112 in FIG. 1) to a distal tip of the delivery element 308. The catheter conductors 320 extend along the longitudinal length of the catheter 302 between the inner layer 322 and the outer layer 324. In at least some embodiments, there is open space between adjacent catheter conductors 320 and between the inner layer 322 and the outer layer 324. In at least some embodiments, the outer layer 324 is flowable during or after application or otherwise changes conformation (e.g., by heat shrinking, or the like) to reduce, or even eliminate open space between adjacent catheter conductors 320 and between the inner layer 322 and the outer layer 324.

Figure 3D:
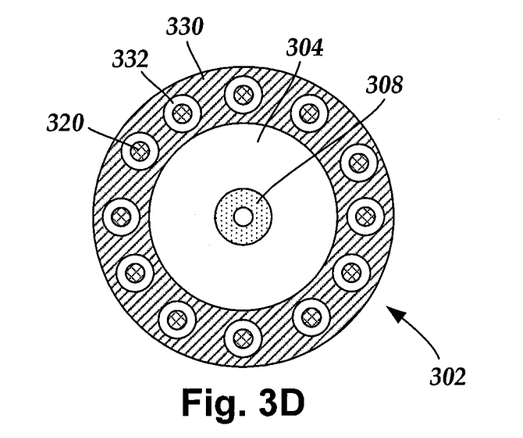
FIG. 3D is a schematic transverse cross-sectional view of another embodiment of a medial portion of the catheter of FIG. 3A, according to the invention.
Figures 4A, 4B, 4C:
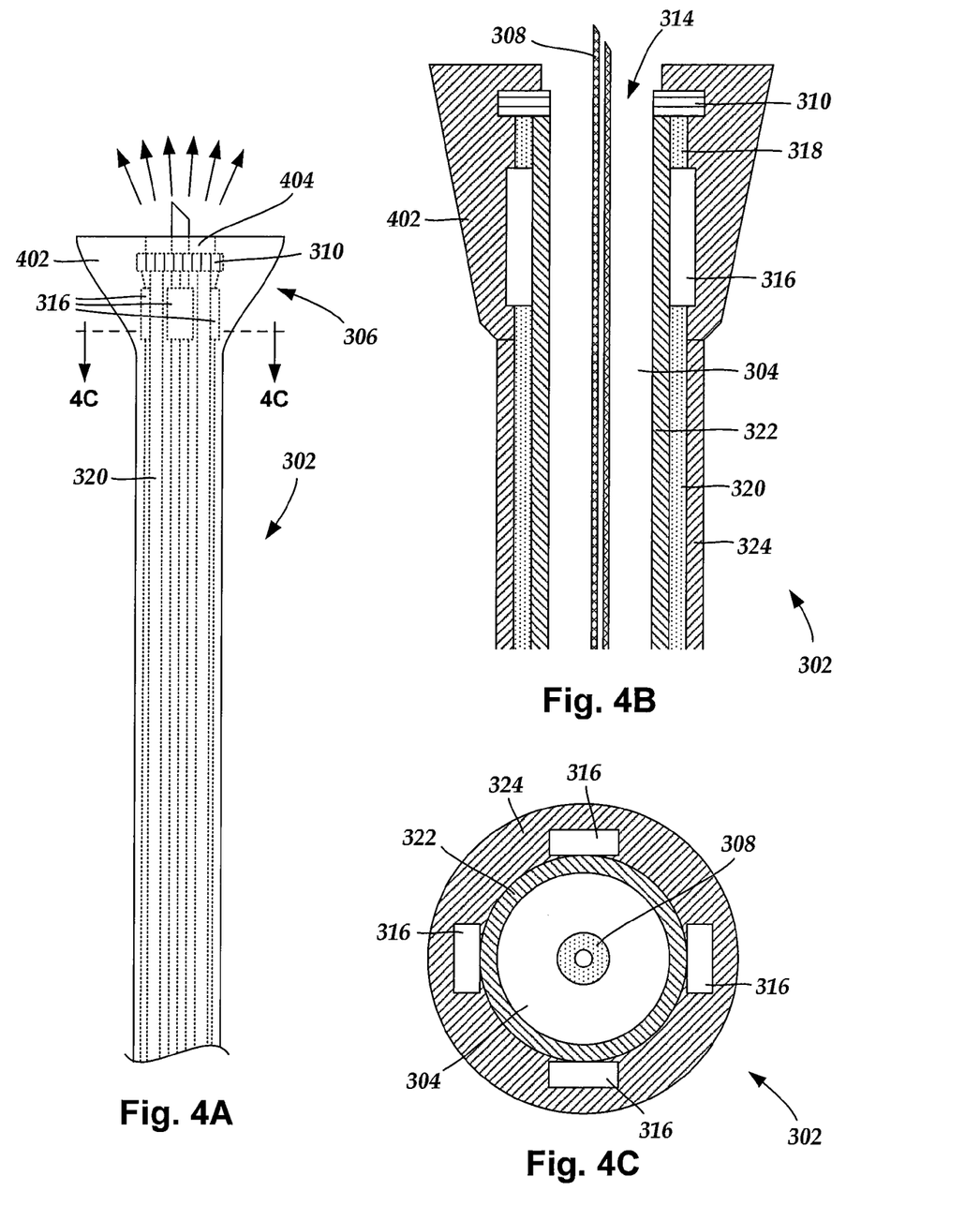
FIG. 4A is a schematic side view of another embodiment of the distal portion of the catheter of FIG. 3A with a flared distal member disposed over the distal tip of the catheter, according to the invention.
FIG. 4B is a schematic longitudinal cross-sectional view of one embodiment of a distal end of the catheter of FIG. 4A, according to the invention.
FIG. 4C is a schematic transverse cross-sectional view of one embodiment of a distal portion of the catheter of FIG. 4A, according to the invention.

In alternate embodiments, the medial portion of the catheter 302 includes a body having one layer of material defining one or more lumens configured and arranged for receiving the catheter conductors 320. FIG. 3D is a schematic transverse cross-sectional view of another embodiment of the medial portion of the catheter 302. The delivery element 308 is disposed in the central lumen 304 of the catheter 302. The catheter 302 includes one layer 330 of material. A plurality of conductor lumens, such as conductor lumen 332, are defined in the layer 330 surrounding the central lumen 304. The conductor lumens 332 are each configured and arranged to receive one or more of the catheter conductors 320. In FIG. 4B, each of the conductor lumens 332 shown are configured and arranged to receive one of the catheter conductors 320. In at least some embodiments, each of the conductor lumens 332 are configured and arranged to receive two or more of the catheter conductors 320. In at least some embodiments, one or more of the conductor lumens 332 is configured and arranged to receive a different number of the catheter conductors 320 than at least one of the remaining conductor lumens 332. It will be understood that, in at least some embodiments, the conductor lumens 332 can be defined in a plurality of layers, instead of a single layer 330.

In at least some embodiments, the catheter 302 includes a flared distal member disposed over the distal tip 306 of the catheter 302. In at least some embodiments, the flared distal member is flared such that a distal end of the flared distal member has a diameter that is greater than a diameter of the transducer array 310. In at least some embodiments, at least a portion of the flared distal member extends distally beyond the transducer array 310.

FIG. 4A is a schematic side view of a flared distal member 402 disposed over the distal tip 306 of the catheter 302. FIG. 4B is a schematic transverse cross-sectional view of one embodiment of a distal end of the catheter 302 and flared distal member 402. FIG. 4C is a schematic transverse cross-sectional view of one embodiment of a distal portion of the catheter 302 with the flared distal member 402. In at least some embodiments, the flared distal member 402 is configured and arranged to increase the surface area of the distal-most surface of the catheter 302 to reduce the risk of perforating patient tissue when the distal end of the catheter 302 contacts patient tissue. In at least some embodiments, the flared distal member 402 forms a hood disposed over the transducer array 310. In at least some embodiments, the flared distal member 402 is disposed over at least a portion of the integrated circuits 316. In at least some embodiments, the flared distal member 402 is cone shaped. In at least some embodiments, the flared distal member 402 is formed from a sonolucent material. In at least some embodiments, the flared distal member 402 defines a lumen 404 that at least partially exposes the transducer array 310. In at least some embodiments, the flared distal member 402 is formed from the same material as one or more of the inner layer 322 or the outer layer 324. In at least some embodiments, the flared distal member 402 is formed by injection molding.

The transducer array 310 defines a central aperture 314 that at least partially aligns with the lumen 304 such that the delivery element 308 can extend from the lumen 304 through the central aperture 314. In at least some embodiments, the transducer array 310 is bonded (e.g., using one or more adhesives, or the like) to one or more of the flared distal member 402 or the inner layer 322. In at least some embodiments, the transducer array 310 is coupled to the catheter 302 by the flared distal member 402 being injection molded around at least a portion of the transducer array 310. In at least some embodiments, one or more of the integrated circuits 316 are bonded (e.g., using one or more adhesives, or the like) to one or more of the flared distal member 402 or the inner layer 322.

The integrated circuits 316 are disposed on an outer surface of the inner layer 322 and the outer layer 324 is disposed over the integrated circuits 316 and the inner layer 322. FIG. 4C shows four integrated circuits. It will be understood that the there may be many different numbers of integrated circuits including, for example, one, two, three, four, five, six, seven, eight, nine, ten, twelve, sixteen, twenty, or more integrated circuits. Other numbers of integrated circuits may be used as well. In at least some embodiments, the integrated circuits 316 are bonded (e.g., using one or more adhesives, or the like) to the inner layer 322.

Figure 5:
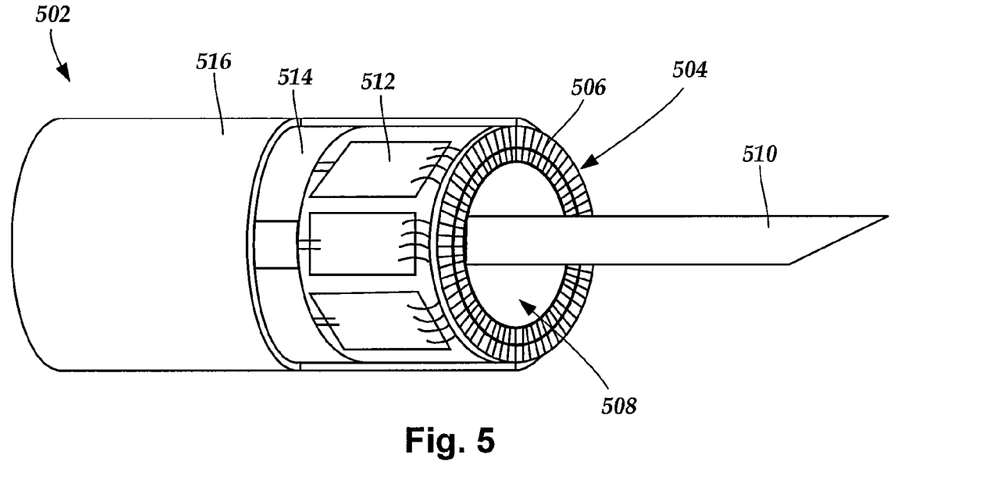
FIG. 5 is a schematic perspective view of one embodiment of a distal end of a catheter with material removed from a portion of the catheter to expose integrated circuits, according to the invention.

FIG. 5 is a schematic perspective view of one embodiment of a distal end of a catheter 502. The catheter 502 includes an annular transducer array 504 that includes a plurality of imaging elements, such as imaging element 506. The transducer array 504 is disposed at a distal end of a lumen 508 defined in the catheter 502. In FIG. 5, the transducer array 504 is shown having two transducer arrays, one for transmitting and one for receiving. A delivery element 510 is disposed in the lumen 508 such that a distal portion of the delivery element 510 extends through the center of the transducer array 504. Integrated circuits 512 are disposed on the catheter 502 and electrically coupled to the transducer array 504 and also to a processor (106 in FIG. 1). The catheter 502 includes a plurality of layers 514 and 516 of material. In at least some embodiments, the plurality of layers contain the electrical wires (e.g., catheter conductors 320) within the walls of the catheter so they do not encumber the advancement of the catheter or the delivery element during a procedure. In at least some embodiments, the plurality of layers protect electrical wiring during the advancement, withdrawal, and other movements of the catheter during a procedure. In at least some embodiments, the plurality of layers increase the catheter profile at the distal tip to reduce the risk of vessel dissection or ventricle perforation. FIG. 5 shows the layers 514 and 516 removed from over top of the integrated circuits 512 for clarity of illustration. In at least some embodiments, however, one or more of the layers 514 and 516 are at least partially disposed over the integrated circuits 512.

Figure 6:
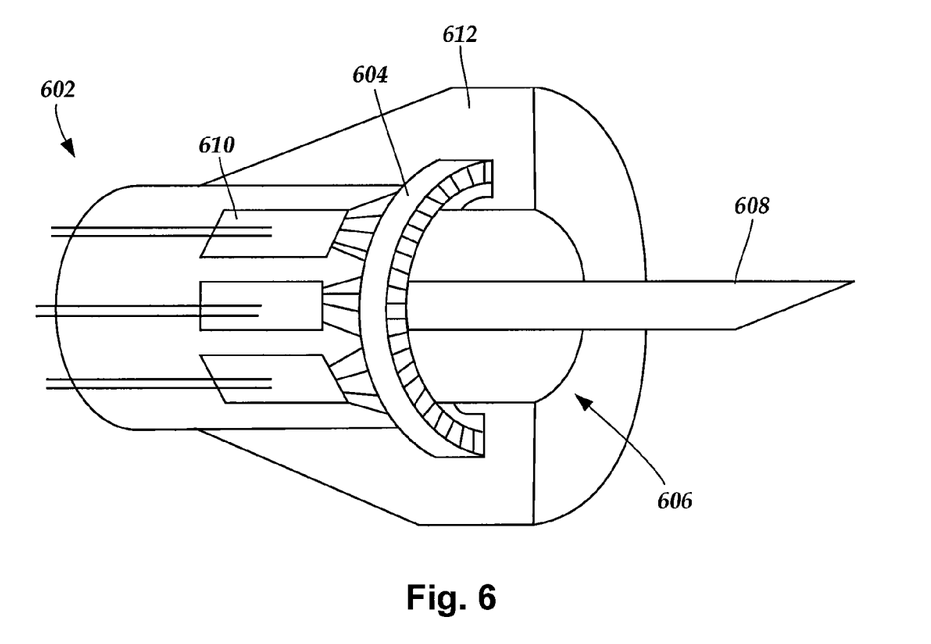
FIG. 6 is a schematic perspective view of one embodiment of a distal end of a catheter with a partial cross-sectional view of a flared distal member disposed over a distal tip of the catheter, according to the invention.

FIG. 6 is a schematic perspective view of one embodiment of a distal end of a catheter 602. The catheter 602 includes an annular transducer array 604 disposed at a distal end of a lumen 606 defined in the catheter 602. A delivery element 608 is disposed in the lumen 606 such that a distal portion of the delivery element 608 extends through the center of the transducer array 604. Integrated circuits 610 are disposed on the catheter 602 and electrically coupled to the transducer array 604 and also to a processor (106 in FIG. 1). The catheter 602 includes a flared distal member 612 disposed over at least a portion of the transducer array 604 and the integrated circuits 610. In FIG. 6, a portion of the flared distal member 612 has been removed, for clarity of illustration. FIG. 6 also does not include any layers of material disposed over the integrated circuits 610, for clarity of illustration.

As discussed above, the transducer array 310, 504, and 604 may be mounted to the distal tip of the catheter 302, 502, and 602 and employed to transmit and receive acoustic signals. In a preferred embodiment, an array of imaging elements (see e.g., imaging element 506 in FIG. 5) are mounted to the catheter. In other embodiments, a single transducer may be employed. Any number of imaging elements can be used. For example, there can be two, three, four, five, six, seven, eight, nine, ten, twelve, fifteen, sixteen, twenty, twenty-five, fifty, one hundred, five hundred, one thousand, or more imaging elements. As will be recognized, other numbers of imaging elements may also be used.

The transducer array may be formed from one or more known materials capable of transforming applied electrical pulses to pressure distortions on the surface of the one or more elements, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

Ultrasound transducers can also be manufactured by semiconductor processes to produce cMUTs. These transducers are tiny diaphragm-like devices with electrodes that convert the sound vibration of a received ultrasound signal into a modulated capacitance. For transmission, a capacitive charge is modulated to vibrate the diaphragm of the device and thereby transmit a sound wave. Since these devices are manufactured by semiconductor processes, the devices can have dimensions in the 10-200 µm range. However, many such devices can be grouped together and operated in unison as a single imaging element.

Pressure distortions on the surface of the one or more imaging elements form acoustic pulses of a frequency based on the frequency of the pressure variation. The resonant frequencies of the imaging elements may be affected by the size, shape, and material used to form the imaging elements. The imaging elements may be formed in any shape suitable for positioning within the catheter and for propagating acoustic pulses of a desired frequency in one or more selected directions. For example imaging elements may be disc-shaped, block-shaped, rectangular-shaped, oval-shaped, and the like. The imaging elements may be formed in the desired shape by any process including, for example, dicing, dice and fill, machining, microfabrication, and the like.

In at least some embodiments, the imaging elements of a transducer array emit acoustic pulses. When an emitted acoustic pulse with sufficient energy encounters one or more medium boundaries, such as one or more tissue boundaries, a portion of the emitted acoustic pulse is reflected back to the emitting imaging element as an echo pulse. Each echo pulse that reaches an imaging element with sufficient energy to be detected is transformed to an electrical signal in the receiving transducer. The one or more transformed electrical signals are transmitted to the control module (104 in FIG. 1) where the processor (106 in FIG. 1) processes the electrical-signal characteristics to form a displayable image of the imaged region based, at least in part, on a collection of information from each of the acoustic pulses transmitted and the echo pulses received.

The quality of an image produced at different depths from the transducer array may be affected by one or more factors including, for example, bandwidth, transducer focus, beam pattern, as well as the frequency of the acoustic pulse. The frequency of the acoustic pulses output from the transducer array may also affect the penetration depth of the acoustic pulse output from the transducer array. In at least some embodiments, the transducer array is configured and arranged to form an image from data collected from a location at least 0.6 cm in front of the transducer array. In at least some embodiments, the transducer array is configured and arranged to form an image from data collected from a location at least 0.8 cm in front of the transducer array. In at least some embodiments, the transducer array is configured and arranged to form an image from data collected from a location at least 1 cm in front of the transducer array. In at least some embodiments, the transducer array is configured and arranged to form an image from data collected from a location at least 1.2 cm in front of the transducer array.

In general, as the frequency of an acoustic pulse is lowered, the depth of the penetration of the acoustic pulse within patient tissue increases. In at least some embodiments, the transducer array operates within a frequency range of 5 MHz to 60 MHz. In at least some embodiments, the transducer array operates at a frequency of at least 5 MHz. In at least some embodiments, the transducer array operates at a frequency of at least 10 MHz. In at least some embodiments, the transducer array operates at a frequency of at least 15 MHz. In at least some embodiments, the transducer array operates at a frequency of at least 20 MHz. In at least some embodiments, the transducer array operates at a frequency of at least 25 MHz.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter assembly comprising:
    a catheter having a distal end with a distal tip, a proximal end, and a longitudinal length, the catheter comprising
        a body that defines a central lumen extending along the catheter to the distal end, the body comprising an inner layer of material and an outer layer of material disposed over the inner layer of material, wherein the inner layer of material is formed electrically-nonconductive material,
        a forward-facing transducer array disposed at the distal tip of the catheter, the transducer array configured and arranged for transforming applied electrical signals to acoustic signals and also for transforming received echo signals to electrical signals,
        at least one catheter conductor electrically coupled to the transducer array and extending along the body; and
        a flared, sonolucent distal member disposed over at least a portion of the transducer array and bonded to the transducer array; and
    a delivery element disposed in the central lumen of the body, the delivery element comprising a distal tip configured and arranged for contacting patient tissue, wherein the distal tip of the delivery element is configured and arranged to extend beyond the distal tip of the catheter.

2. The catheter assembly of claim 1, wherein the delivery element defines at least one lumen.

3. The catheter assembly of claim 2, wherein the lumen of the delivery element is in fluid communication with a therapeutic source.

4. The catheter assembly of claim 1, wherein the distal tip of the delivery element is configured and arranged to pierce patient tissue when the distal tip contacts patient tissue.

5. The catheter assembly of claim 1, wherein the flared distal member defines a lumen through which the delivery element is at least partially exposed.

6. The catheter assembly of claim 1, wherein the transducer array is annular.

7. The catheter assembly of claim 1, wherein the transducer array comprises a plurality of capacitive micromachined ultrasonic transducer imaging elements and at least one integrated circuit electrically coupled to the capacitive micromachined ultrasonic transducer imaging elements.

8. The catheter assembly of claim 1, wherein the transducer array is flush with an outer surface of the outer layer of material, 9. The catheter assembly of claim 1, wherein the at least one catheter conductor is disposed between the inner layer and the outer layer, 10. The catheter assembly of claim 1, wherein the integrated circuits are disposed between the inner layer and the outer layer.

11. An intravascular and endocardial therapy system comprising:
the catheter assembly of claim 1; and
a control module coupled to the transducer array, the control module comprising
a pulse generator configured and arranged for providing electric signals to the transducer array, the pulse generator electrically coupled to the transducer array of the catheter assembly via the at least one catheter conductor, and
a processor configured and arranged for processing received electrical signals from the transducer array to form at least one image, the processor electrically coupled to the transducer array via the at least one catheter conductor.

12. The intravascular and endocardial therapy system of claim 11, wherein the delivery element defines at least one lumen.

* * * * *